(12) United States Patent
DeWitt et al.

(10) Patent No.: US 6,566,520 B2
(45) Date of Patent: *May 20, 2003

(54) SUPPORT FOR SYNTHESIS AND PURIFICATION OF COMPOUNDS

(75) Inventors: Sheila Helen DeWitt, Stockton, NJ (US); Robert Ramage, Edinburgh (GB); Alasdair Arthur MacDonald, San Mateo, CA (US)

(73) Assignee: Warner-Lambert Company, Morris Plains, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 153 days.

(21) Appl. No.: 09/291,524

(22) Filed: Apr. 14, 1999

(65) Prior Publication Data

US 2003/0077651 A1 Apr. 24, 2003

Related U.S. Application Data

(62) Division of application No. 09/048,166, filed on Mar. 25, 1998, now Pat. No. 5,977,400.
(60) Provisional application No. 60/041,618, filed on Mar. 27, 1997.

(51) Int. Cl.[7] ..................... C07D 401/00; C07D 215/12
(52) U.S. Cl. ......................... 544/363; 544/51; 544/156; 560/51; 422/99; 422/100; 422/101; 422/102; 422/103; 422/104; 422/131; 435/300; 435/301; 530/333; 530/334; 546/156; 546/174; 546/176
(58) Field of Search ............................ 560/51; 544/363, 544/156, 51; 422/131, 99–104; 435/300–301, DIG. 22; 530/333, 334; 546/156, 174, 176

(56) References Cited

U.S. PATENT DOCUMENTS 5,324,483 A * 6/1994 Cody et al. .................. 422/131
5,977,400 A * 11/1999 DeWitt et al.

OTHER PUBLICATIONS

Hacplus Abstract: Hay et al., "Use of Tetrabenzo[a,c,g,i] Fluorene as an Anchor Group Towards the Synthesis of Ciprofloxacin," Innovation Perspect. Solid Ohase Synth. Comb. Libr., Collect. Pap., Int. Symp., 5th, Meeting Date: Sep. 1997, pp. 235–238. E and copy of reference, 1999.*

MacDonald et al., "A Solid Phase Approach to Quinolines Using the DIVERSOMER Technology," Tetrahedron Lett., vol. 37, No. 27, 4815–4818, 1996.*

Ramage et al., "Design of An Affinity–Based N–alpha–amino Protecting Group for Peptide Synthesis: Tetrabenzo[a,c,g,i]Fluorenyl–17–Methyl Urethanes (Tbfmoc), "Tetrahedron Lett., vol.33, No. 3, 385–38,. 1992.*

* cited by examiner

Primary Examiner—Bennett Celsa
(74) Attorney, Agent, or Firm—Merchant & Gould P.C.

(57) ABSTRACT

A method for the preparation and purification of compounds using a novel support, a tetrabenzo [a, c, g, i]-fluorene group (Tbf) comprising reacting a building block (A) containing a Tbf group (Tbf-A), with a second building block (B), to afford an intermediate compound (Tbg-A-B) followed by purifying the intermediate compound by adsorption on a carbon support, removing the intermediate compound from the support with a solvent and repeating the previous reactions using the required number of building blocks to synthesize the compounds followed by removal of the Tbf group to afford the desired compounds.

2 Claims, 1 Drawing Sheet

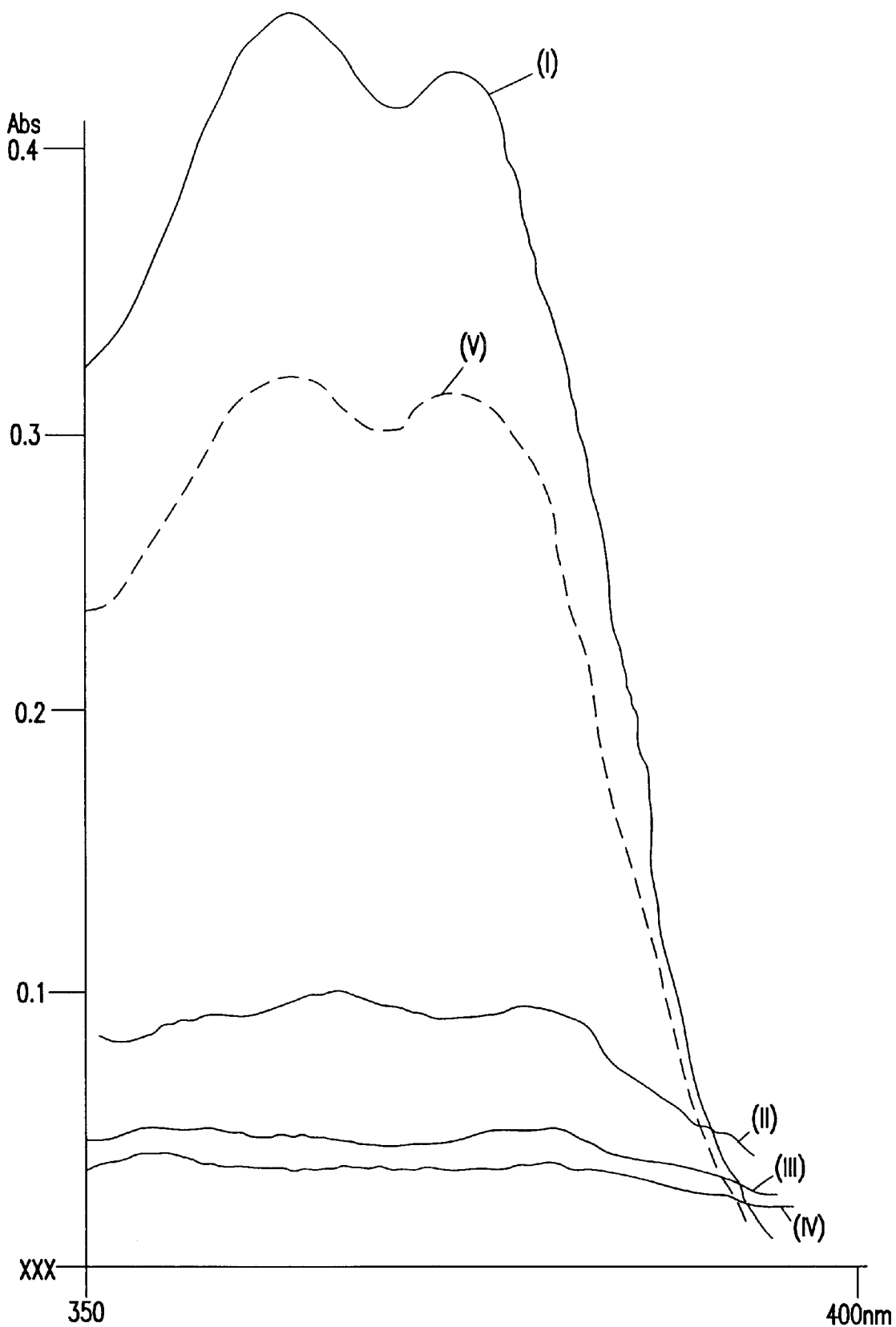

SUPPORT FOR SYNTHESIS AND PURIFICATION OF COMPOUNDS

CROSS REFERENCE TO RELATED APPLICATIONS

This application is a divisional of U.S. patent application Ser. No. 09/048,166, filed Mar. 25, 1998, now U.S. Pat. No. 5,977,400, which claims priority to U.S. Provisional Application Ser. No. 60/041,618, filed Mar. 27, 1997.

BACKGROUND OF THE INVENTION,

The present invention relates to a method for the preparation and purification of compounds employing a novel support. More particularly, the present invention relates to a method for preparing and purifying a library of compounds useful as pharmaceutical agents using a tetrabenzo [a, c, g, i]-fluorene group (Tbf).

A key step in any drug development program is the identification of a lead compound suitable for clinical trials. Increasing competitiveness in the pharmaceutical market and escalating costs for discovery efforts have placed extreme demands on the pharmaceutical industry. The search for new drugs has generally relied on traditional medicinal chemistry approaches which are both time consuming and costly.

The discovery and development of a new drug takes on average 12 years, at an estimated cost of $357 million (Pharmaceutical Manufacturers Association, "Facts at a Glance", 1993). Recently, advances in high throughput synthesis (HTS) and laboratory automation have resulted in the synthesis of medicinal compounds becoming a rate limiting step in the drug discovery process.

Traditional methods for the generation and evaluation of large numbers of compounds have relied heavily on natural products, fermentation broths, marine organisms, and recombinant and chemically synthesized peptides. Combinatorial chemistry is a synthetic strategy by which large, diverse libraries of compounds can be created and has added to the pool of compound sources available at present in the pharmaceutical industry (Früchtel J. S., Jung G., *Angew. Chem. Int. Ed. Engl.,* 1996;35:17). The advent of combinatorial chemistry has provided a means for the preparation of hundreds, or even thousands of diverse chemical libraries at a fraction of the normal cost and time.

A recent phenomenon, combinatorial chemistry has resulted in the successful preparation of peptides and oligonucleotide based libraries (Gallop M. A., Barrett R. W., Dower W. J., Foder S. P., Gordon E. M., *J. Med. Chem.,* 1994;37:1232). This new field of chemistry has also been expanded to small organic molecules such as the benzodiazepines (Hobbs DeWitt S., Schroeder M. C., Stankovic C. J., Cody D. M. R., Pavia M. R., *Proc. Natl. Acad. Sci. USA,* 1993;90:6909; Ellman J. A., Bunin B. A., *J. Am. Chem. Soc.,* 1992;114:10997) and hydantoins (Hobbs DeWitt S., Schroeder M. C., Stankovic C. J., Cody D. M. R., Pavia M. R., *Proc. Natl. Acad. Sci. USA,* 1993;90:6909). Consistent with this trend, most of the top selling drugs on the market are low molecular weight, heterocyclic compounds.

To date, combinatorial strategies have primarily concentrated on solid phase synthesis (SPS) methodologies. Historically, SPS has focused on the preparation on biopolymers such as peptides and oligonucleotides by the use of a few well-characterized chemical transformations to generate repetitive structural backbones. In comparison, SPS of small molecule targets is not fully understood; however, the inherent advantages of the methodology over traditional solution based methods has resulted in the development of solid phase organic synthesis (SPOS).

A variety of solid supports have been described for SPS, most notably the use of functionalised cross-linked polystyrene. Typically, excess reagents are readily tolerated by the solid support, reactions generally show favorable kinetics and can be driven to completion, product isolation is improved by washing away excess reagents from the solid support, and no purification of reaction intermediates is required.

The selection and use of polystyrene resins is, however, dependent upon compatibility with the reaction route necessary to synthesize the target molecule, as well as the method of attachment and cleavage from the solid support. Mechanical and thermal stability of the solid support should also be considered in combination with the method of agitation and the temperature range of the synthetic route. Furthermore, the presence of entrapped impurities and resin by-products can impact the final product yields and purities (MacDonald A. A., DeWitt S. M., Ghosh S., Hogan E. M., Kieras L., Czarnik A. W., Ramage R., Molecular Diversity, 1996;3:183–186).

In order to circumvent the problems associated with solid phase synthesis, there has been some work in the area of generating libraries of compounds using traditional solution phase methodologies. A major drawback of this approach is the general requirement for purification of reaction intermediates which can be both costly and time consuming, particularly if a library of compounds is being prepared.

One method that utilizes the advantages of both solid phase synthesis and solution phase synthesis has been the development of tetrabenzo [a, c, g, i] fluorene (Tbf) and its affinity to porous graphitized carbon (PGC) which was developed by Ramage R., et al., in the late 1980s (Ramage R., Raphy G., *Tetrahedron Lett.,* 1992; 33:385)

The general concept involves tagging the N-terminus of a peptide chain with a suitable aromatic derivatized protecting group. Subsequently, the tag is selectively adsorbed on to PGC. Truncated peptides are then removed by washing, and the final pure peptide can be obtained by deprotection and elution from PGC.

The introduction of solid phase peptide synthesis (SPPS) by Merrifield in 1963 greatly simplified the task of peptide synthesis. Yet one of the main obstacles of SPPS is the difficulty of purification of the final product due to the accumulation of truncated peptides on the resin. Several chromatographic separation methods are available for purification, one of which involves affinity based purification with PGC.

PGC has a porous two-dimensional graphite structure with a large surface area available for affinity binding. More importantly, PGC has strong hydrophobic adsorption with unique selectivity, particularly to aromatic systems. In order to exploit this hydrophobic interaction which PGC exhibited for large, flat molecules, Ramage and Raphy set out to design a new, planar, aromatic system for the purification of peptides (Ramage R., Raphy G., *Tetrahedron Lett.,* 1992;33:385).

In 1960, Martin, et al., reported the first synthesis of Tbf (de Ridder R., Martin R. H., *Bull. Soc. Chim. Belg.,* 1960;69:534); however, the chemistry of Tbf received little attention until 1988 when Ramage and Raphy synthesized three derivatives of Tbf as potential intermediates in the synthesis of N-Tbfmoc amino acids and peptides. In addition to the strong fluorescent properties of Tbf, it also exhibited strong hydrophobic binding to PGC. Ramage, et al., have successfully applied this technique to the design of a highly hydrophobic N-amino protecting group and a 5'-hydroxyl protecting group for peptide and DNA synthesis, respectively. It was found to be useful in the final purification step either by selective binding to PGC, or as a hydrophobic chromatographic label to allow HPLC based purification.

A key component in the synthesis of appropriate protecting groups has been the reactivity of the methylene bridge at position 17 of the Tbf molecule. The hydrogen atoms are highly acidic which is attributed to the high stability of the resonance stabilized cyclopentadienyl anion generated under basic conditions.

With these unique properties in mind, we have surprisingly and unexpectedly found that by utilizing the charcoal/Tbf affinity interaction such an approach could be used in the generation of compounds and in particular a library of compounds using, for example, the Diversomer® Technology disclosed in U.S. Pat. No. 5,324,483 which is herein incorporated by reference. Analogous to SPOS, such a system can be used to replace the standard polystyrene based solid supports with charcoal. Thus, the chemistry of Tbf derivatives are modified depending on the synthetic scheme, and all reactions are carried out in solution phase. While this eliminates the problems associated with SPS, the use of charcoal as a solid support could be introduced at the end of each stage in the synthesis to purify the intermediates and final product(s).

SUMMARY OF THE INVENTION

Accordingly, a first aspect of the present invention is a method for the synthesis of a compound which comprises:

Step (a) treating a building block containing a tetrabenzo [a, c, g, i] fluorene group (Tbf-A), with a second building block (B), in a solvent to afford an intermediate compound (Tbf-A-B);

Step (b) purifying the intermediate compound (Tbf-A-B), by adsorption on a carbon-like support;

Step (c) removing the intermediate compound (Tbf-A-B), from the support with a solvent or optionally by heating in a solvent;

Step (d) repeating Steps (a)–(c) using the required number of building blocks to synthesize a compound containing a Tbf group; and Step (e) removing the Tbf group from the compound by adsorption on a carbon-like support and subsequently adding a cleaving reagent in a solvent to afford the desired compound.

A second aspect of the present invention is a method for the multiple, simultaneous synthesis of compounds which comprises:

Step (a) treating a building block containing tetrabenzo [a, c, g, i] fluorene group (Tbf-A), with a second building block (B), in a solvent to afford an intermediate compound (Tbf-A-B);

Step (b) purifying the intermediate compound (Tbf-A-B), by adsorption on a carbon-like support;

Step (c) removing the intermediate compound (Tbf-A-B), from the support with a solvent or optionally by heating in a solvent;

Step (d) repeating Steps (a)–(c) using the required number of building blocks to synthesize a series of compounds containing Tbf groups; and Step (e) removing the Tbf groups from the compounds by adsorption on a carbon-like support and subsequently adding a cleaving reagent in a solvent to afford the desired compounds.

A third aspect of the present invention is a method for the multiple, simultaneous synthesis of compounds using an apparatus which comprises:

Step (a) charging the apparatus with a building block containing a tetrabenzo [a, c, g, i] fluorene group (Tbf-A);

Step (b) treating Tbf-A with a second building block (B), in a solvent to afford an intermediate compound (Tbf-A-B);

Step (c) purifying the intermediate compound (Tbf-A-B), by adsorption on a carbon-like support;

Step (d) removing the intermediate compound (Tbf-A-B), from the support with a solvent or optionally by heating in a solvent;

Step (e) repeating Steps (b)–(d) using the required number of building blocks to synthesize a series of compounds containing Tbf groups; and Step (f) removing the Tbf groups from the compounds by adsorption on a carbon-like support and subsequently adding a cleaving reagent in a solvent to afford the desired compounds.

A fourth aspect of the present invention is a novel compound which is [4-[[10-(17H-tetrabenzo-[a, c , g, i] fluoren-17-yl)decyl]oxy]phenyl]methyl 2,4,5-trifluoro-β-oxobenzenepropanoate and which is useful in the preparation of ciprofloxacin.

A fifth aspect of the present invention is a novel compound which is [4-[[10-(17H-tetrabenzo [a, c, g, i]-fluoren-17-yl)decyl]oxy]phenyl]methyl α-[(cyclopropylamino)methylene]-2,4,5-trifluoro-β-oxobenzenepropanoate and which is useful in the preparation of ciprofloxacin.

A sixth aspect of the present invention is a novel compound which is [4-[[10-(17H-tetrabenzo [a, c, g, i]-fluoren-17-yl)decyl]oxy]phenyl]methyl 1-cyclopropyl-6,7-difluoro-1,4-dihydro-4-oxo-3-quinolinecarboxylate and which is useful in the preparation of ciprofloxacin.

A seventh aspect of the present invention is a novel compound which is [4-[[10-(17H-tetrabenzo-[a, c, g, i] fluoren-17-yl)decyl]oxy]phenyl]methyl 1-cyclopropyl-6-fluoro-1,4-dihydro-4-oxo-7-(1-piperazinyl)-3-quinolinecarboxylate and which is useful in the preparation of ciprofloxacin.

DETAILED DESCRIPTION OF THE INVENTION

In this invention, the term "building block" means a reagent used to build (synthesize) a compound such as, for example, a starting material used in the synthesis of a compound.

"Carbon-like support" means a type of carbon which strongly adsorbs aromatic systems such as, for example, charcoal, and the like.

"Cleaving reagent" means a reagent used to specifically cleave the desired compound(s) from the Tbf moiety.

"PIN(S)" means a reaction tube having an upper and lower end whereby the lower end comprises a filter which can hold a solid material.

"Compound" means both inorganic and organic materials such as, for example, oligosaccharides, aromatic and non-aromatic heterocycles, aromatic carbocycles, alicycles, and the like.

The term "aromatic heterocycle" means a heteroaromatic ring which is thiophene, furane, pyrrole, imidazole, pyrazole, thiazole, isothiazole, oxazole, isoxazole, 1,2,4-triazole, 1,2,3-triazole, tetrazole, pyridine, pyridazine, pyrazine, pyrimidine, quinoline, isoquinoline, indole, benzo

[b]thiophene, benzoxazole, benzimidazole, benzothiazole, unsubstituted or substituted by 1 to 2 substituents selected from alkyl straight or branced having from 1 to 12 carbon atoms, phenyl, naphthyl, alkoxy, thioalkoxy, ie, o-alkyl or s-alkyl, as defined above for alkyl, hydroxy, thiol, nitro, halogen as defined hereinafter, formyl, amino,

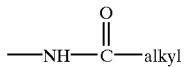

wherein alkyl is as defined above,

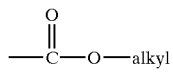

wherein alkyl is as defined above,

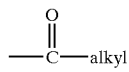

wherein alkyl is as defined above or phenyl.

The term "halogen" means fluorine, chlorine, bromine or iodine.

The term "nonaromatic heterocyclic" means 5-7 membered saturated heterocyclic ring optionally interrupted by a second heteroatom selected from nitrogen, oxygen and sulfur such as, for example, pyrrolidine, pyrrazolidine, imidazolidine, oxazolidine, thiaoxazolidine, piperidine, piperazine, morpholine, thiamorpholine, homopiperidine, and the like. When the second heteroatom is nitrogen as, for example, an imidazolidine or piperazine, said nitrogen atom may be substituted by alkyl, carboxyalkyl or lower alkyl-carboxyalkyl as defined above for alkyl. The carbon atoms of the above 5-7 membered heterocyclic ring may be substituted independently by alkyl, amino, aminoalkyl, monoalkylaminoalkyl, dialkylaminoalkyl, carboxy, carboxyalkyl, alkylcarboxyalkyl, thio, thioalkyl, alkylthioalkyl, hydroxy, hydroxyalkyl, alkoxy or alkoxyalkyl (alkyl and alkoxy are as defined above) or a 5-7 membered saturated or monounsaturated carbocyclic ring optionally fused to a benzene ring such as, for example, cyclopentane, cyclopentene, cyclohexane, cyclohexene, cycloheptane, cycloheptene, indane, tetralin and benzosuberane or a 5,6 or 6,6-membered bicyclic carbocyclic rings such as, for example, bicyclo [3.2.1] octane or bicyclo [2.2.2] octane or a 5-7 membered saturated heterocyclic ring optionally fused to a benzene ring such as, for example, the "5-7 membered saturated heterocyclic ring optionally interrupted by a second heteroatom selected from nitrogen, oxygen and sulfur" as defined above and, in addition, dihydrobenzofuran, dihydroisobenzofuran, dihydrobenzothiophene, dihydroisobenzothiophene, indoline, isoindoline, chroman, isochroman, thiochroman; isothiochroman, tetrahydroquinoline, tetrahydroisoquinoline, and the like or a 5,6 or 6,6-membered heterocyclic bicyclic rings such as, for example, 1-aza-bicyclo [3,2,1] octane or 1-aza-bicyclo [2.2.2] octane.

The term "aromatic carbocycle" means an aromatic ring which is benzene, naphthalene and the like, unsubstituted or substituted by 1 to 4 substituents selected from alkyl as defined above, alkoxy as defined above, thioalkoxy as defined above, hydroxy, thiol, nitro, halogen, amino,

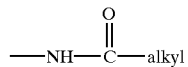

wherein alkyl is as defined above,

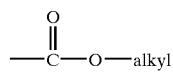

wherein alkyl is as defined above,

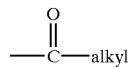

wherein alkyl is as defined above, phenyl or naphthyl.

The term "alicycle" means a saturated hydrocarbon ring which contains from 3 to 12 carbon atoms, for example, cyclopropane, cyclobutane, cyclopentane, cyclohexane, adamantane, and the like.

The following table provides a list of abbreviations and definitions thereof used in the present invention.

| Abbreviation | Solvents, Reagents, and Instrumentation |
|---|---|
| 9-BBN | 9-Borobicyclo[3.3.1]nonane |
| CDCl$_3$ | Deuterated chloroform |
| CHCl$_3$ | Chloroform |
| DCM (or CH$_2$Cl$_2$) | Dichloromethane |
| DIBAL—H | Diisobutyl aluminum hydride |
| DMAP | 4-Dimethylaminopyridine |
| DMF | Dimethylformamide |
| DMF:DMA | Dimethylformamide dimethyl acetal |
| EIMS | Electron impact mass spectroscopy |
| Et$_3$N | Triethylamine |
| FABMS | Fast atom bombardment mass spectroscopy |
| FTIR | Fourier transform infrared spectroscopy |
| H$_2$O | Water |
| H$_2$O$_2$ | Hydrogen peroxide |
| HCl | Hydrogen chloride |
| HCO$_2$Me | Methylformate |
| HRMS | High resolution mass spectroscopy |
| m | Multiplet (NMR) |
| MeOH | Methanol |
| MgSO$_4$ | Magnesium sulfate |
| n-BuLi | n-Butyl lithium |
| Na$_2$CO$_3$ | Sodium carbonate |
| NaOH | Sodium hydroxide |
| NMR ($^1$H NMR) | Proton nuclear magnetic resonance spectroscopy |
| NMP | N-methyl-2-pyrrolidinone |
| PGC | Porous graphitized carbon |
| ppm | Parts per million |
| rt | Room temperature |
| s | Singlet (NMR) |
| t | Triplet (NMR) |
| Tbf | Tetrabenzo[a,c,g,i]fluorene |
| TFA | Trifluoroacetic acid |
| THF | Tetrahydrofuran |
| TLC | Thin layer chromatography |
| TMG | 1,1,3,3-Tetramethyl guanidine |
| UV | Ultra violet spectroscopy |

The preparation of a compound according to the first aspect of the present invention is shown in Scheme 1. Thus, a building block, A, is reacted with Tbf :in a solvent such as, for example, DCM and the like to afford an intermediate compound Tbf-A which is subsequently purified by adsorption on a carbon-like support such as, for example, charcoal, and the like. The intermediate compound, Tbf-A is then removed from the support with a solvent such as, for example, toluene and the like or optionally by heating in a solvent such as, for example, toluene and the like. The previous procedure is repeated sequentially adding building blocks B and C to afford a compound ABC containing a Tbf group. The Tbf group, containing compound ABC, is removed from the compound by adsorption on a carbon-like support followed by addition of a cleaving reagent such as, for example, sodium hydroxide/ethanol and the like to afford the desired pure compound (ABC).

The preparation of compounds according to the second and third aspects of the present invention is illustrated by the following general procedure.

Thus, for the multiple simultaneous synthesis of compounds, either manual or automated procedures may be employed. For example, a Diversomer® apparatus, as disclosed in U.S. Pat. No. 5,324,483 which is incorporated by reference can be used to prepare a library of compounds. A general procedure comprising 8 or 40 reaction vessels using this apparatus employs the following steps:

1. The apparatus is set up consisting of an aluminum reservoir block containing reservoir vials to which solvents, preferably 3 to 5 mL, and reagents are added.

2. The PINS consisting of a frited cup are placed in the teflon holder block which is attached to the aluminum reservoir block. The manifold is attached, and the apparatus is ready for use.

3. Reactions can be carried out under inert atmosphere by the introduction of nitrogen or argon gas via the inlet. Additionally, chilled nitrogen gas can also be introduced via the inlet valve allowing for refluxing of the apparatus.

4. At the start of a synthetic route, each reservoir vial, generally referred to as vials is charged with a building block containing a tetrabenzo [a, c, g, i] fluorene group (Tbf-A). A reagent(s), (B) is added in a solvent and the first step of the synthesis carried out.

5. Following completion of the first step,,the crude solutions in the vials are dried to remove excess solvent. Subsequently, the crude residue (Tbf-A-B) is dissolved in another solvent, preferably a protic solvent such as methanol.

6. To each PIN, a carbon support such as charcoal is added and the PINS immersed in the solution. Adsorption of the Tbf moiety to charcoal can be monitored by UV analysis at 360 to 400 nm.

7. The holder block containing the PINS is then removed from the vials and placed in a clean set of vials. An alternative solvent such as toluene is added to each vial and the complete apparatus left to stand, sonicated, or heated, with agitation for a period of time. Subsequent desorption of Tbf-A-B from charcoal can be monitored by UV analysis.

8. At this point, each of the PINS containing the carbon support can be removed from the holder block and replaced with new PINS. The solution in the vials can be dried and the next step of the synthesis attempted by addition of appropriate reagents (C) and solvent to the vials.

9. Steps (5)–(7) can be repeated using the required number of building blocks to synthesize a library of compounds containing Tbf groups.

10. The compounds containing the Tbf groups can then be removed by adsorption on charcoal and subsequently a cleaving reagent added in a solvent to afford the desired pure library of compounds in solution and the Tbf moiety attached to the carbon solid support.

11. The desired library will consist of pure compounds in solution ready for full chemical and biological analysis.

SCHEME 1

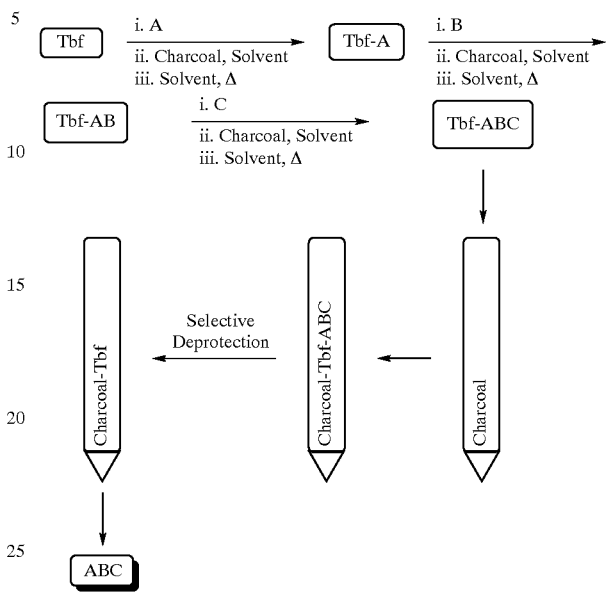

Scheme 2 shows the preparation of a starting material, i.e., a functionalized Tbf moiety, 17H-tetrabenzo [a, c, g, i] fluorene-17-propan-3-ol.

Scheme 3 shows the use of 17H-tetrabenzo-[a,c, g, i] fluorene-17-propan-3-ol to prepare 3-(17H-tetrabenzo [a, c, g, i] fluoren-17-yl)propyl-2,4,5-trifluoro-β-oxobenzenepropanoate (Tbf-bound β-keto ester). The Tbf-bound β-keto ester can subsequently be converted to a quinolone.

Scheme 4 shows studies of the binding affinity of the Tbf-bound β-keto ester.

Scheme 5 shows the preparation of a series of quinolone anti-infective agents according to the method of the present invention.

The preparation of a specific quinolone anti-infective agent, i.e., 1-cyclopropyl-6-fluoro-1,4-dihydro-4-oxo-7-(1-piperazinyl)-3-quinolinecarboxylic acid, 1, also known as ciprofloxacin disclosed in U.S. Pat. No. 4,670,444 which is incorporated by reference according to the method of the present invention is described in Scheme 6.

Thus, the bromo-ester, 10, was synthesized from ethyl 4-hydroxy benzoate, 11, and 1,10-dibromodecane in 63% yield. Preferably a three-fold molar-excess of 1,10-dibromodecane was used in order that only mono-substitution was obtained.

Coupling of the bromo-ester, 10, to Tbf was achieved by first forming the tetrabutylammonium salt of 8bH-Tbf, 13. Tetrabutylammonium hydroxide (Bu₄NOH) was added to a refluxing solution of 13 in degassed dioxane. The bright yellow salt, 12, was then isolated by filtration and refluxed immediately with bromo-ester, 10, in degassed dioxane to form ethyl 4-[[10-(17H-tetrabenzo [a, c, g, i] fluoren-17-yl)decyl]oxy]-benzoate, 9, in a good overall yield of 68.

The ester, 9, was reduced using an excess of diisobutylaluminum hydride (DIBAL-H) forming 4-[[10-(17H-tetrabenzo [a, c, g, i] fluoren-17-yl)decyl]oxy]-benzenemethanol, 8, in an excellent yield of 94%.

Coupling of 7, to Tbf-alcohol, 8, was achieved by transesterification using catalytic N,N-dimethylamino-pyridine (DMAP) in refluxing toluene (Taber D. F., *J. Org. Chem,* 1985;50:3618). Approximately a three-fold excess of 7 was employed in order to drive the reaction to completion and afford [4-[[10-(17H-tetrabenzo [a, c, g, i] fluoren-17-yl)

decyl]oxy]phenyl]-methyl 2,4,5-trifluoro-β-oxobenzenepropanoate, 6, in 49% yield.

The quinolone, [4-[[10-(17H-tetrabenzo [a, c, g, i]-fluoren-17-yl)decyl]oxy]phenyl]methyl 1-cyclopropyl-6,7-difluoro-1,4-dihydro-4-oxo-3-quinolinecarboxylate, 3, was formed in three steps from Tbf-ketoester, 6. The first step of the synthesis involved reaction with DMF-DMA (R=methyl, ethyl). The intermediate enamide, 5, was reacted in situ with cyclopropylamine to form [4-[[10-(17H-tetrabenzo [a, c, g, i]fluoren-17-yl)decyl]-oxy]phenyl]methyl α-[(cyclopropylamino)methylene]-2,4,5-trifluoro-β-oxobenzenepropanoate, 4. Cyclization was achieved by refluxing 4 with a base, tetramethylquanidine (TMG), to afford Tbf-quinolone, 3.

Tbf-quinolone, 3, was converted to Tbf-ciprofloxacin, 2, using piperazine in pyridine.

Characteristic absorbencies were observed at 336 nm, 323 nm, and 281 nm.

Cleavage of the desired ciprofloxacin, 1, from the anchor group can be carried out with trifluoroacetic acid (TFA) by stirring 2 in a solution of TFA/DCM of varying concentration.

The following nonlimiting examples illustrate the inventor's preferred method for carrying out the method of the present invention.

SCHEME 2

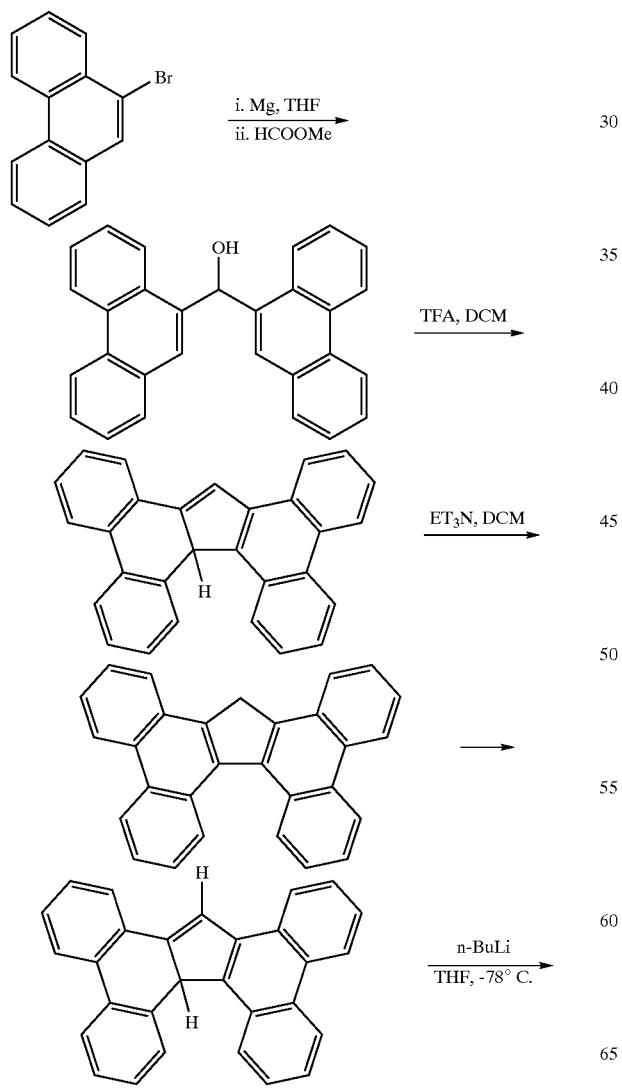

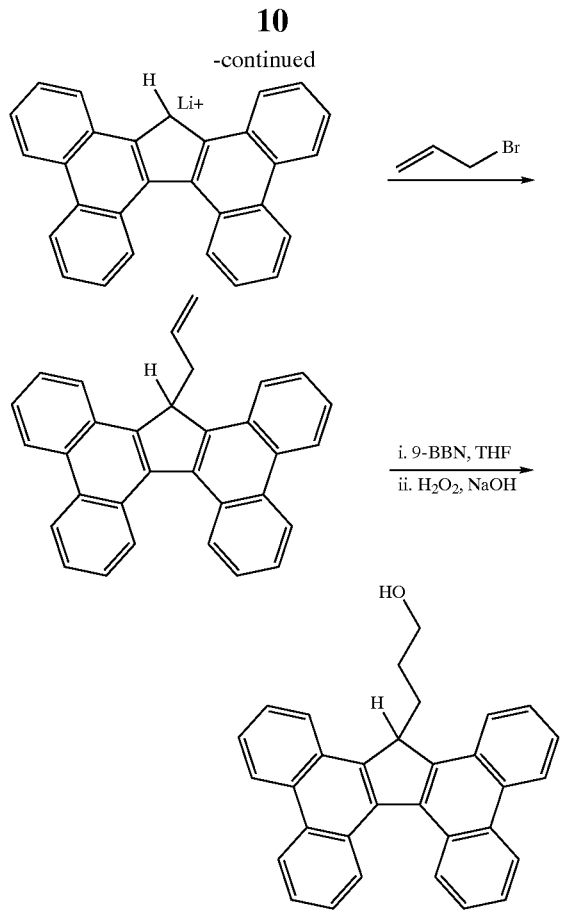

SCHEME 3

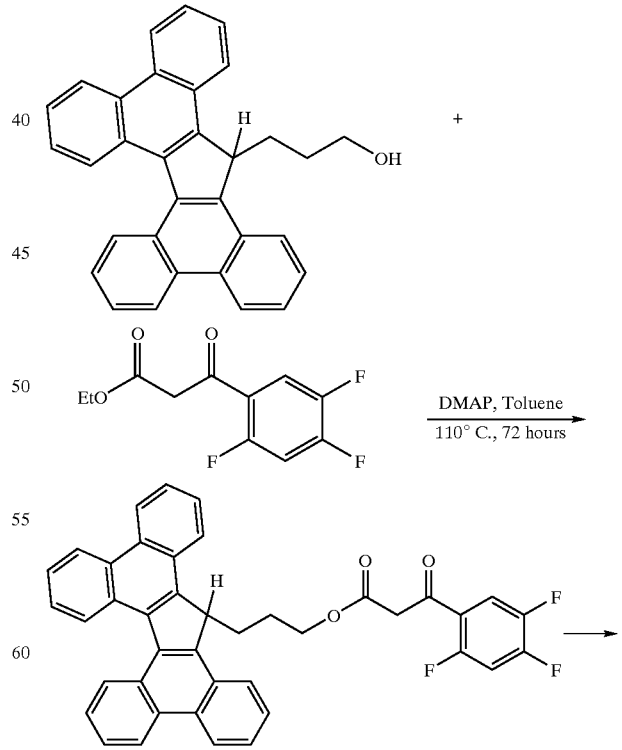

SCHEME 4
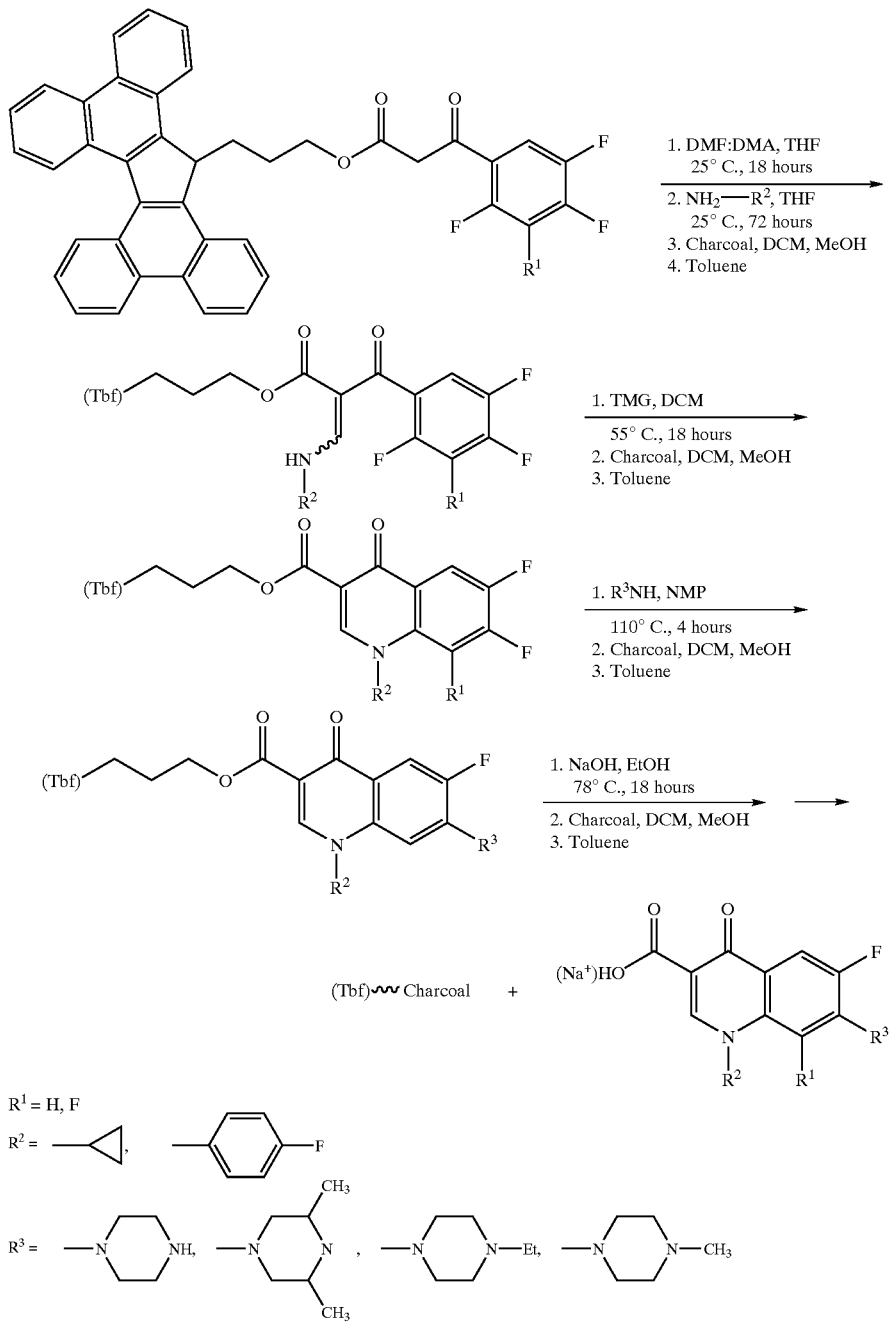
SCHEME 5
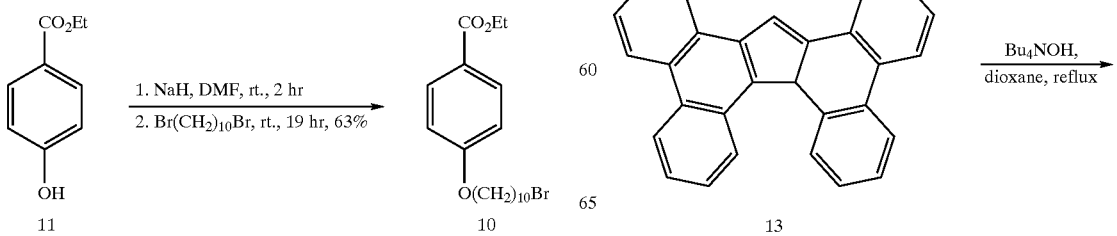

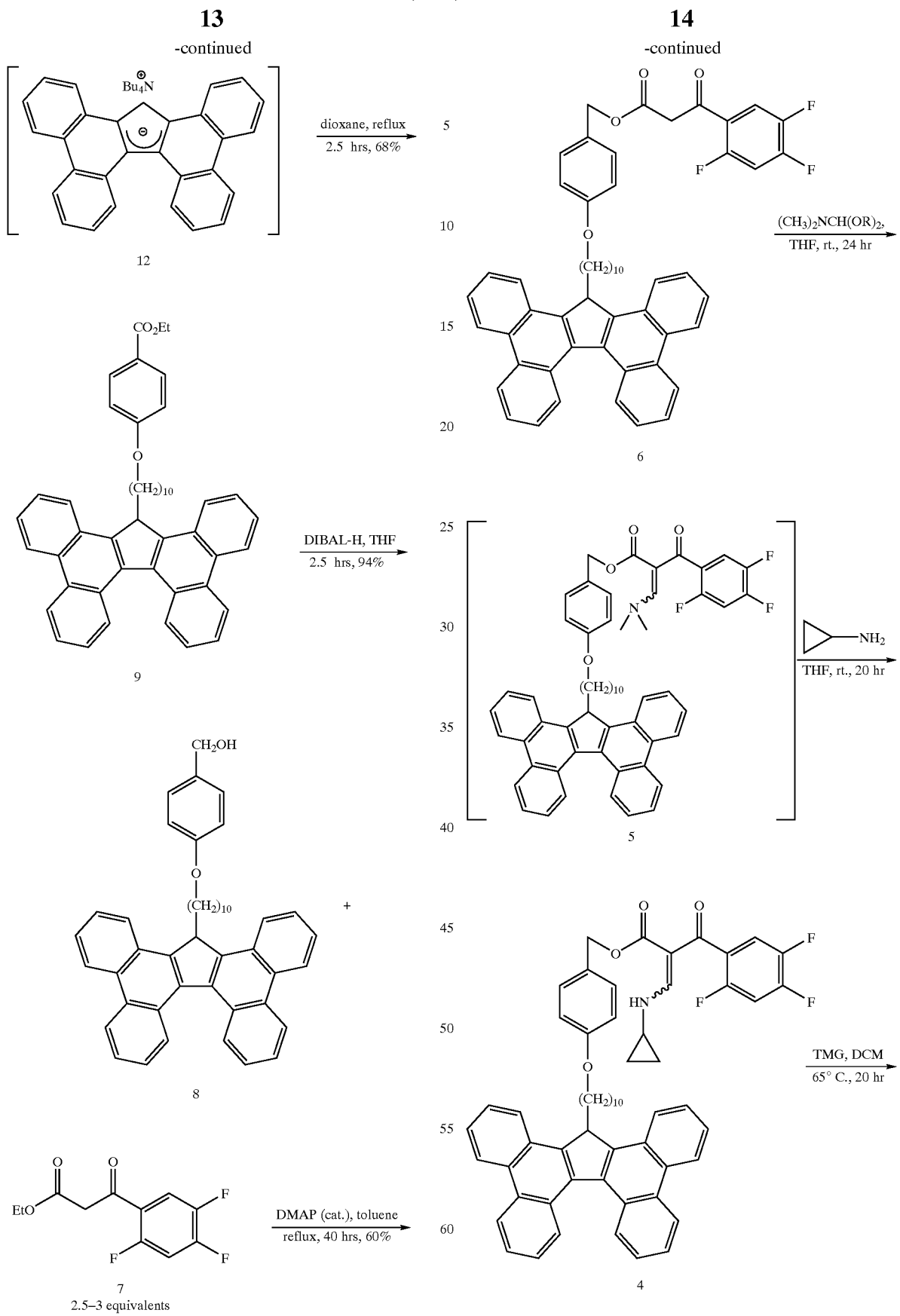

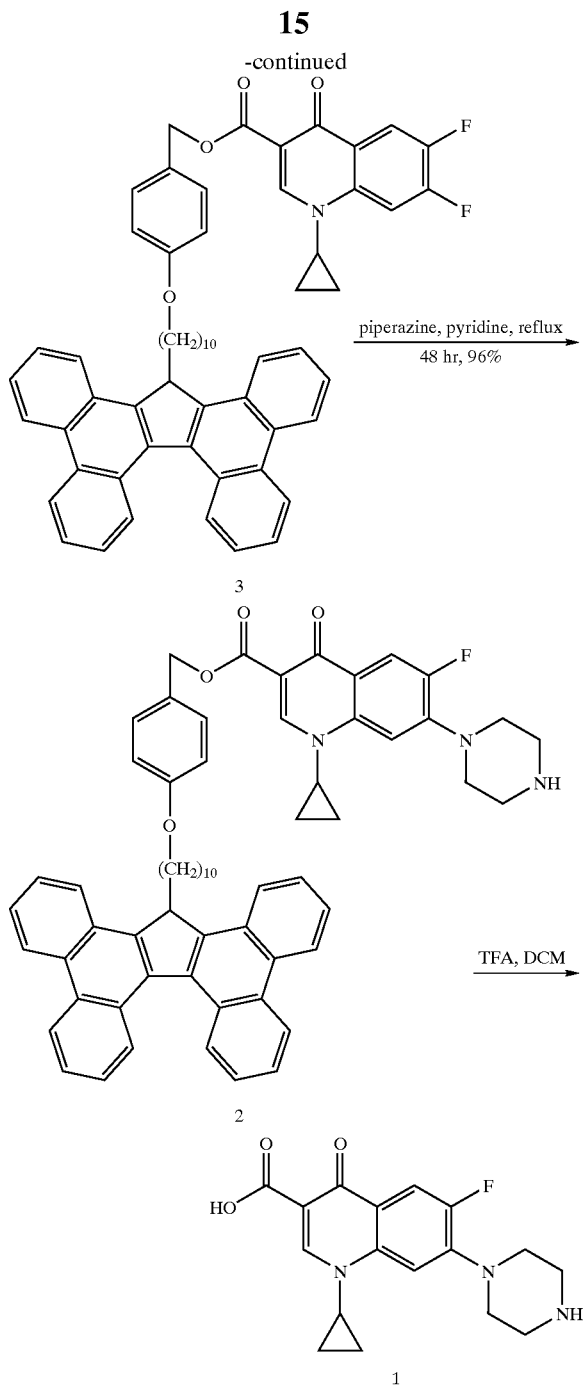

presence of the Tbf chromophore between the range 400 to 350 nm. Following the addition of PCG (40 mg), the Tbf/PGC mixture was agitated and centrifuged. Ultraviolet analysis of the supernatant confirmed 80% adsorption of the product onto PGC. This was further increased to 90% adsorption by the addition of methanol (2×1 mL), as shown in Scheme 4.

Additionally, the PGC/Tbf binding affinity can be reversed by the addition of toluene (10 mL) which showed 72% desorption of the product from PGC. Subsequently, the desorbed product can be used in additional work such as the synthesis of the quinolones.

EXAMPLE 2

Synthesis of Quinolone Antibacterial Agents Using a Diversomer® Apparatus

17H-Tetrabenzo [a, c, g, i] fluorene-17-propan-3-ol (0.12 g, 0.28 mmol) was added to eight reaction vials and dissolved in toluene (5 mL). A catalytic amount of DMP and 3-oxo-3-(2,4,5-trifluoro-phenyl)-propionic acid ethyl ester (0.20 g, 0.84 mmol) were added to each of the vials. The holder block containing the PINS was attached followed by the manifold. The apparatus was placed in a sonic bath and heated to 110° C., with cooling of the PINS maintained by the introduction of chilled nitrogen via the inlet valve. After 72 hours, the apparatus was dissembled and the vials dried by nitrogen sparge to remove the toluene. The crude residues were redissolved in DCM (5 mL); PCG (50 mg) was added to each PIN and immersed into the vials containing the DCM solutions. After 30 minutes at room temperature, the PINS and the adsorbed Tbf-β-keto esters (3-(17H-tetrabenzo [a, c, g, i] fluoren-17-yl)propyl 2,4,5-trifluoro-β-oxobenzenepropanoate) were removed, drained, and placed into clean reaction vials containing toluene (5 mL). Following an additional 30 minutes at room temperature, the PINS were removed from the apparatus and the desorbed toluene solutions dried by nitrogen sparge to yield the pure Tbf-bound β-keto esters in vials A1 to B4, respectively.

The pure esters were suspended in a solution of anhydrous THF (3 mL). Dimethylformamide dimethyl acetal (DMF:DMA) (0.12 mL, 1.0 mmol) was added to each vial and the apparatus sonicated at room temperature, for 18 hours, under an atmosphere of nitrogen. To vials A1–A4, cyclopropylamine (0.12 mL, 1.7 mmol) was added, while to vials B1–B4, 4-fluoroaniline (0.19 g, 1.7 mmol) was added. Following agitation in the sonic bath, at 25° C., for a period of 72 hours, the vials were dried by nitrogen sparge and the crude residues redissolved in methanol (5 mL). PGC (50 mg) was added to each PIN and the PINS immersed in the methanol solutions A1 to B4, respectively. Following 30 minutes at room temperature, the PINS containing the Tbf-bound enamides were removed from the methanol solutions and placed into reaction vials containing toluene (5 mL) Following a further 30 minutes at room temperature, the PINS were removed from the apparatus and the toluene solutions dried to yield the pure Tbf-bound enamides.

Cyclization was achieved by dissolving the enamides in a solution of tetramethylguanidine (TMG), (0.86 mL, 6.4 mmol) and DCM (4 mL), followed by agitation at 55° C., for 18 hours. Subsequently, the solutions were dried, redissolved in methanol (5 mL), adsorbed onto PGC (50 mg) and released into solution to liberate the pure cyclized quinolones. The final site of diversity was introduced by dissolving each of the eight quinolones in N-methyl pyrrolidinone (NMP), (4 mL). To vials A1 and B1, piperazine (0.25 g, 2.86

EXAMPLE 1

Preparation and Binding Affinity Study of a Tbf-Bound β-Ester

17H-Tetrabenzo [a, c, g, i] fluorene-17-propan-3-ol (0.12 g, 0.28 mmol) was dissolved in toluene (20 mL), a catalytic amount of DMAP was added followed by 3-oxo-3-(2,4,5-trifluoro-phenyl)-propionic acid ethyl ester (0.20 q, 0.84 mmol) and the reaction mixture heated to 110° C., for 72 hours. The crude product was purified to yield the pure Tbf-bound β-keto ester in 56% yield. Subsequently, the binding affinity of the Tbf-bound β-keto ester to PGC was studied as a purification prototype to the quinolones.

Initially, the Tbf β-keto ester (1.6 mg) was dissolved in DCM (100 mL) and the UV spectrum measured for the mmol) was added, vials A2 and B2, 2,6-dimethylpiperazine (0.326 g, 2.86 mmol), vials A3 and B3, N-ethyl-piperazine (0.37 g, 2.86 mmol), and to vials A4 and B4, N-methylpiperazine (0.29 g, 2.86 mmol). Subsequently, the apparatus was heated to 110° C. for 4 hours. On drying the acylated quinolones by nitrogen sparge, the crude residues were dissolved in methanol (5 mL) and purified by the normal methodology using PGC to generate the Tbf-bound quinolones in solution.

Finally, sodium hydroxide (0.1 N) in ethanol (5 mL) was added to the Tbf-bound quinolones, A1 to B4 and the vials heated to 78° C., for 18 hours. PGC (50 mg) was added to the PINS and submerged in the reaction vials for 1 hour. Afterwards, the PINS containing PGC-bound Tbf were removed and the pure solutions dried to yield the desired library of eight quinolones.

EXAMPLE 3

1-Cyclopropyl-6-fluoro-1,4-dihydro-4-oxo-7-(1-piperazinyl)-3-quinolinecarboxylic acid Step (a): Preparation of Di-phenanthren-9-yl-methanol Magnesium turnings (4.7 g, 0.196 mol) and a crystal of iodine were charged to an oven-dried, three-necked flask fitted with a dropping funnel and condenser. The system was purged with nitrogen and 9-bromophenanthrene (50.6 g, 0.197 mol) was added to the flask as a solution in dry THF (80 mL), dropwise over a period of 20 minutes. Heat evolved and the reaction mixture turned into a green liquid. After 2.5 hours, methylformate (5.95 g, 0.099 mol) was added as a solution in dry THF (25 mL) over a period of 20 minutes. The reaction mixture turned yellow/brown and was stirred at room temperature under an atmosphere of nitrogen for a further 2 hours. The reaction mixture was then poured onto HCl (2 M, 100 mL), forming a white precipitate. Excess magnesium was destroyed with more HCl. The white precipitate was filtered, washed with diethyl ether, and collected as di-phenanthren-9-yl-methanol (24.5 g, 0.063 mol, 64%). Rf 0.50 (CHCl$_3$), mp 236–238° C. (Wahl F. O. and Ramage R., PhD Thesis, Edinburgh University, 1993). FTIR, $v_{max}$/cm$^{-1}$ 3466, 3055, 1492, 1449, 1248, 1071, 1037, 805, 748, 723. $^1$H NMR (CDCl$_3$, 250 MHz), δ/ppm 8.79–8.67 (4 H, m, Ar H); 8.13–8.10 (2 H, m, Ar H); 7.80–7.50 (12 H, m, Ar, H); 7.31 (1 H, s, CHOH); 2.76 (1 H, s, CHOH). $^{13}$C{$^1$H}NMR (CDCl$_3$, 63 MHz), δ/ppm 136.3, 131.2, 130.8, 130.3, 130.0 (quat. Ar C); 129.0, 126.9, 126.8, 126.6, 126.4, 126.0, 124.3, 123.1, 122.3 (Ar C—H); 69.6 (CH—OH). HRMS (FAB), M$^+$/z C$_{29}$H$_{20}$O requires 384.1514, found 384.1498.

Step (b): Preparation of 1H-Tetrabenzo [a, c, g, i]-fluorene, (13)

Di-phenanthen-9-yl-methanol (24.5 g, 63 mmol) was suspended in CH$_2$Cl$_2$ (100 ml). Trifluoroacetic acid (40 mL) was added dropwise under an atmosphere of nitrogen over a period of 10 minutes, forming a yellow suspension. This was stirred at room temperature under nitrogen for 20 minutes after which time excess solvent was removed in vacuo. The resulting yellow solid was suspended in CH$_2$Cl$_2$ (100 mL) and reconcentrated (5 times). The residue was then washed with diethyl ether to give 1H-tetrabenzo [a, c, g, i] fluorene as a bright yellow solid (16.4 g, 45 mmol, 70%). Rf 0.84 (CHCl$_3$/methanol, 9.1), mp 276–278° C. (Wahl F. O. and Ramage R., PhD Thesis, Edinburgh University, 1993).

FTIR, $v_{max}$/cm$^{-1}$ 3055, 1608, 1442, 865, 740, 721. $^1$H NMR (CDCl$_3$, 250 MHz), δ/ppm 8.81–8.76 (2 H, m, Ar—H); 8.28–7.08 (15 H, m, Ar—H), 5.39 (1 H, s, C—H). $^{13}$C{$^1$H}NMR (CDCl$_3$, 63 MHz), δ/ppm 148.3, 141.3, 137.2, 135.2, 133.7, 130.7, 130.3, 129.3, 127.5, (quat. Ar C); 128.3, 128.2, 127.1, 126.9, 126.6, 126.5, 126.3, 126.2, 125.8, 125.1, 124.9, 124.6, 123.6, 123.5, 123.2, 121.2, (Ar C—H), 53.1 (C—H). $\lambda_{max}$/nm (ε/dm$^3$mol$^{-1}$cm$^{-1}$) 374 (11713), 358 (9883), 301 (31845), 254 (62225). HRMS (FAB), M$^+$/z C$_{29}$H$_{18}$ requires 366.1409, found 366.1396.

Step (c.) Preparation of 4-(10-Bromo-decyloxy)-benzoic acid ethyl ester, (10)

Sodium hydride (1.55 g, 61 mmol) was suspended in DMF (150 mL) under an atmosphere of nitrogen. Ethyl-4-hydroxybenzoate (11) (5.06 g, 30 mmol) was added as a solution in DMF (30 mL) via syringe which was then washed with DMF (2×5 mL). The reaction mixture was then stirred at room temperature under an atmosphere of nitrogen for 2 hours. After this time, 1,10-dibromodecane (30.84 g, 103 mmol) was added as a solution in DMF (50 mL) via syringe which was then washed with DMF (2×5 mL). The reaction mixture was then stirred at room temperature under nitrogen for 19 hours. The reaction was quenched with water (200 mL) and the organic fragments extracted with diethyl ether (4×150 mL), dried over MgSO$_4$, and excess solvent removed in vacuo to form a colorless oil. This was purified by flash column chromatography using CH$_2$Cl$_2$/hexane (1:1) to CH$_2$Cl$_2$/hexane (3:1) as eluting solvents to form a white crystalline solid. This was recrystallized from ethanol to form 4-(10-bromo-decyloxy)-benzoic acid ethyl ester (7.38 g, 19.1 mmol, 63%). Rf 0.65 (CH$_2$Cl$_2$), mp 41–42° C. FTIR, $v_{max}$/cm$^{-1}$ 1 3023, 2927, 2855, 1708, 1604, 1509, 1468, 1390, 1367, 1312, 1252, 1155, 1018, 851, 772. $^1$H NMR (CDCl$_3$, 250 MHz), δ/ppm 7.96 and 6.87 (both 2 H, m, Ar—H); 4.32 (2 H, q, $^3$J=7.1 Hz, –CH$_2$CH$_3$); 3.97 (2 H, t, $^3$J=6.5 Hz, —OCH$_2$—); 3.38 (2 H, t, $^3$J=6.9 Hz, —CH$_2$Br); 1.80 (4 H, m, —OCH$_2$CH$_2$— and —CH$_2$CH$_2$Br); 1.42–1.27 (15 H, m, alkyl C—H). $^{13}$C{$^1$H} NMR (CDCl$_3$, 63 MHz), δ/ppm 166.2 (C=O); 152.6 and 122.4 (quat. Ar C); 131.3 and 113.8 (Ar C—H); 67.9 and 60.4 (—OCH$_2$—); 33.9, 32.6, 29.2, 29.1, 29.0, 28.9, 28.5, 28.0, 25.8 (CH$_2$); 14.2 (—CH$_3$) $\lambda_{max}$/nm (ε/dm$^3$mol$^{-1}$cm$^{-1}$) 257 (24641). HRMS (FAB), M$^+$/z C$_{19}$H$_{30}$BrO$_3$ (MH$^+$) requires 385.1378, found 385.1374.

Step (d) Preparation of Ethyl 4-[[10-(17H-tetrabenzo [a, c, g, i] fluoren-17-yl) decyl]oxy]benzoate, 9

1H-Tetrabenzo [a, c, g, i] fluorene (13) (2.08 g, 5.68 mmol) was suspended in degassed dioxane 80 mL) and heated to reflux under an atmosphere of nitrogen. Tetrabutylammonium hydroxide (40% w/w in H$_2$O, 3.50 g, 5.41 mmol) was added as a solution in dioxane (20 mL) via syringe which was then washed with dioxane (2×5 mL). A yellow precipitate formed immediately which was filtered under nitrogen and washed with warm dioxane (100 mL) and diethyl ether (100 mL). The salt was resuspended in dioxane (100 mL) and to it added 4-(10-bromo-decyloxy)-benzoic acid ethyl ester (10) (2.08 g, 5.40 mmol). The reaction mixture was refluxed under an atmosphere of nitrogen after which time a dark solution had formed. Solvent was removed in vacuo to form a dark brown oil. This was dissolved in diethyl ether and the supernatant removed to leave a yellow slurry. This was washed with diethyl ether (233 30 mL) and all the diethyl ether extracts combined and concentrated. The resulting residue was purified by flash column chromatography using CH$_2$Cl$_2$/hexane (1:1) as the eluting solvent. The product was isolated as a pale yellow airy solid which was washed with and concentrated from diethyl ether four times. The desired product was precipitated from diethyl ether as a pale yellow powder (2.46 g, 3.67 mmol, 68%). Rf 0.71 (CH$_2$Cl$_2$), mp 122–124° C. FTIR, $v_{max}$/cm$^{-1}$ 3072, 2922, 2850, 1702, 1605, 1505, 1454, 1423, 1355, 1277, 1252, 1165, 1105, 1021, 849, 756, 727. $^1$H NMR (CDCl$_3$, 200 MHz), δ/ppm 8.81 and 8.68 (both 6 H, m, Ar—H); 8.23–8.18 (2 H, m, Ar—H); 8.06–7.98 (2 H, m, Ar—H); 7.72–7.58 (8 H, m, Ar—H); 6.93–6.82 (2 H, m, Ar—H), 4.92 (1 H, t, $^3$J=4.2 Hz, CHCH$_2$—); 4.39 (2 H, q, $^3$J=7.1 Hz, OCH$_2$CH$_3$); 3.86 (2 H, t, $^3$J=6.5 Hz, —OCH$_2$—); 2.60–2.52 (2 H, m, —OCH$_2$CH$_2$—); 1.67–0.34 (19 H, m, alkyl H). $^{13}$C{$^1$H} NMR (CDCl$_3$, 50 MHz), δ/ppm 166.3 (C=O); 162.7, 122.4 (quat. Ar C); 131.3, 113.8 (Ar CH); 144.2, 136.6, 131.1, 130.2, 128,6, 127.9 (quat. Tbf Ar C); 127.3, 126.6, 125.7, 125.4, 124.8, 124.3, 123.3 (Tbf Ar CH); 67.9, 60.4 (—OCH$_2$—), 47.0 (allylic C); 29.2, 28.9, 28.8, 28.6, 25.5, 22.0 (—CH$_2$—); 14.2 (—CH$_3$). λ$_{max}$/nm (ε/dm$^3$mol$^{-1}$cm$^{-1}$) 381 (20688), 365 (20967), 301 (45848), 256 (86944). HRMS (FAB), M$^+$/z C$_{48}$H$_{46}$O$_3$ (M$^+$) requires 670.3447, found 670.3447.

Step (e) Preparation of 4-[[10(17H-tetrabenzo-[a, c, g, i] fluorene-17-yl) decyl]oxy]benzenemethanol, 8

Ethyl 4-[[10-(17H-tetrabenzo [a, c, g, i] fluoren-17-yl) decyl]oxy]benzoate (9) (2.03 g, 3.03 mmol) was charged to an oven-dried flask along with freshly distilled THF (40 mL) and the resultant solution stirred at room temperature under an atmosphere of nitrogen. Diisobutyl aluminum hydride (12.0 mL, 12.00 mmol) was added via syringe and the resulting mixture stirred at room temperature under nitrogen for 2 hours, after which time, TLC analysis showed that all the starting material had been consumed. The reaction was quenched with the addition of HCl (2 M, 40 mL), and the organic products were extracted with ethyl acetate (3×5 mL), washed with saturated Na$_2$CO$_3$ (40 mL) and water (40 mL), and dried over MgSO$_4$. Excess solvent was removed in vacuo to yield 4-[[10-(17H-tetrabenzo [a, c, g, i] fluoren-17-yl)decyl]oxy]-benzenemethanol (1.7765 g, 2.82 mmol, 94%). Rf 0.35 (CH$_2$Cl$_2$), mp 64–66° C. FTIR, ν$_{max}$/cm$^{-1}$ 3460, 2920, 2854, 1609, 1510, 1420, 1244, 1171, 1142, 1042, 849, 764, 728. $^1$H NMR (CDCl$_3$, 250 MHz), δ/ppm 8.82 and 8.78 (4 H, m, Tbf Ar—H); 8.77–8.69 (2 H, m, Tbf Ar—H); 8.24–8.20 (2 H, m, Tbf Ar—H); 7.72–7.60 (8 H, m, Tbf Ar—H); 7.27–7.60 (2 H, m, Ar—H); 6.86–6.83 (2 H, m, Ar—H); 4.93 (1 H, t, $^3$J=4.3 Hz, CHCH$_2$—; 4.59 (1 H, s, CH$_2$OH); 3.81 (2 H, t, $^3$J=6.5 Hz, —OCH$_2$—); 2.61–2.56 (2 H, m, —OCH$_2$CH$_2$—); 1.87 (1 H, s, OH); 1.64–0.35 (17 H, m, alkyl H). $^{13}$C{$^1$H}NMR (CDCl$_3$, 63 MHz) δ/ppm 158.5, 132.6 (quat. Ar C); 128.4, 114.2 (Ar CH); 144.2, 136.6, 127.8, 131.0, 130.2, 128.6, 127.8 (quat. Tbf Ar C); 127.3, 126.6, 125.7, 125.4, 124.8, 124.3, 123.3, 123.3 (Tbf Ar CH); 67.7 (—OCH$_2$—); 64.8 (—CH$_2$OH); 47.0 (allylic C); 33.3, 29.2, 29.0, 28.9, 28.6, 25.6, 22.0 (—CH$_2$—). λ$_{max}$/nm (δ/dm$^3$mol$^{-1}$cm$^{-1}$) 381 (18418), 365 (18836), 301 (41440), 254 (70741). HRMS (FAB), M$^+$/z C$_{46}$H$_{44}$O$_2$ (M$^-$) requires 628.3341, found 628.3339.

Step (f) Preparation of 3-oxo-3-(2,4,5-trifluoro-phenyl)-propionic acid ethyl ester, 7

To an oven-dried flask was added potassium ethyl malonate (3.66 g, 21.5 mmol) and freshly distilled acetonitrile (70 mL). The mixture was cooled to 10° C. to 15° C. and stirred under an atmosphere of nitrogen and to it added anhydrous magnesium chloride (2.44 g, 25.7 mmol) and triethylamine (2.05 g, 20.3 mmol). The mixture was then stirred at room temperature under nitrogen for 2.5 hours. The resultant white slurry was recooled to 0° C. and 2,4,5-trifluorobenzoyl chloride was added over a period of 15 minutes, followed by more triethylamine (0.23 g, 2.3 mmol). The mixture was then stirred at room temperature overnight under nitrogen. Acetonitrile was then removed in vacuo and toluene (30 mL) was added. The mixture was reconcentrated and more toluene (60 mL) then added. Hydrochloric acid (1.5 M, 40 mL) was cautiously added, ensuring that the temperature did not exceed 25° C., and the aqueous layer separated. The organic fraction was washed with 1.5 M HCl (2×25 mL) and water (2×25 mL), dried over MgSO$_4$, and solvent removed in vacuo to afford 3-oxo-3-(2,4,5-trifluoro-phenyl-propionic acid ethyl ester as a pale orange solid (2.35 g, 9.55 mmol, 94%). Rf 0.55 (CH$_2$C$_2$), mp 57–59° C. FTIR, ν$_{max}$/cm$^{-1}$ 3088, 2990, 1735, 1687, 1514, 1429, 1321, 1205, 1140, 1055, 897, 807. $^1$ H NMR (CDCl$_3$, 250 MHz), δ/ppm [12.69 (s), 5.81 (s) and 3.92 (d, J=3.9 Hz)] (2 H, keto-enol tautomers); 7.74 (1 H, m, Ar H); 6.98 (1 H, m, Ar H); 4.24 and 4.17 (2 H, both q, $^3$J=7.1 Hz); 1.31 and 1.24 (3 H, both t, $^3$J=7.1 Hz). $^{13}$C{$^1$ H}NMR (CDCl$_3$, 63 MHz), δ/ppm 187.8 (C=O); 173.0 (—HC=C); 166.9 (CO$_2$Et); 163.7, 159.8, 155.9, 151.8, 149.0, 145.3, 120.9 (quat. Ar C); 118.7, 106.6 (Ar C—H); 92.9 (HC=C); 61.4 and 60.6 (—OCH$_2$); 49.4 (—OCCH$_2$CO—); 14.0 (—CH$_3$). $^{19}$FNMR (CDCl$_3$, 235 MHz) δ/ppm –110.6 and –111.7 (m, Ar F); –123.5 and –129.0 (m, Ar F); –140.5 and –141.7 (m, Ar F). λ$_{max}$/nm (δ/dm$^3$mol$^{-1}$cm$^{-1}$) 295 (4781), 281 (3962), 240 (5191). HRMS (EI), M$^+$/z C$_{11}$H$_9$F$_3$O$_3$ (M$^-$) requires 246.0504; found 246.0514.

Step (g): Preparation of [4-[[10-(17H-Tetrabenzo-[a, c, g, i] fluoren-17-yl-decyl]oxy]phenyl]methyl 2,4,5-trifluoro-β-oxobenzenepropanoate, 6

4-[[10-(17H-Tetrabenzo [a, c, g, i] fluoren-17-yl)decyl] oxy]benzenemethanol (8) (44.9 mg, 0.071 mmol) and DMAP (3.2 mg, 0.026 mmol) were added to an oven-dried flask and dissolved in freshly distilled toluene (8 mL). 3-Oxo-3-(2,4,5-trifluoro-phenyl)-propionic acid ethyl ester (7) (46.2 mg, 0.19 mmol) was added and the resultant solution refluxed under an atmosphere of nitrogen for 20 hours. The reaction was cooled to room temperature and solvent removed in vacuo to yield an orange oil. This was dissolved in DCM/methanol (3:2, 25 mL). Charcoal (prewashed with toluene, 510 mg) was added and the suspension stirred at room temperature for 15 minutes. Methanol was added in portions (total 45 mL) and stirring continued until TLC analysis showed that none of the desired product was present in the supernatant liquid. The supernatant was removed by centrifugation and the charcoal residue then suspended in toluene (40 mL). The suspension was then stirred at 40° C. for 15 minutes and the supernatant removed by centrifugation. This was repeated with fresh toluene until no fluorescent products were detected in the supernatant by TLC. The toluene washes were combined and solvent removed in vacuo. The yellow residue was purified by flash column chromatography using DCM as eluent to yield the desired product (35.2 mg, 60%). Rf 0.53 (CH$_2$Cl$_2$), mp 58–60° C. FTIR, ν$_{max}$/cm$^{-1}$ 3089, 3061, 2933, 2853, 1737, 1690, 1619, 1513, 1428, 1331, 1170, 1139, 848, 823. $^1$ H NMR (CDCl$_3$, 250 MHZ), δ/ppm [12.69 (s), 5.86 (s), and 3.95 (d, J=3.9 Hz)] (2 H, keto-enol tautomers); 8.82–8.76 (4 H, m, Ar H); 8.72–8.68 (2 H, m, Ar H); 8.25–8.22 (2 H, m, Ar—H): 7.82–7.59 (9 H, m, Ar H); 7.33–7.22 (2 H, m, Ar—H); 6.95–6.80 (3 H, m, Ar—H); 5.13 (2 H, s, —OCH$_2$—Ar); 4.97 (1 H, t, $^3$J=4.3 Hz, allylic H); 3.83 (2 H, t, $^3$J=6.6 Hz, —OCH$_2$); 2.64–2.55 (2 H, m, —OCH$_2$CH$_2$—); 1.67–0.35 (16 H, m, alkyl H). $^{13}$C{$^1$H}NMR (CDCl$_1$, 63 MHz), δ/ppm 187.6 (C=O); 172.8 (—HC=C); 166.7 (CO$_2$Et); 159.2, 126.8 (quat. Ar C); 163.7, 159.8, 155.9, 151.8, 149.0, 145.3, 120.9 (quat. Ar C); 144.2, 136.6, 131.1, 130.2, 128.7, 127.9 (Tbf quat. Ar C); 130.0, 114.3 (Ar CH); 118.4, 106.5 (Ar CH); 127.3, 126.6, 125.7, 125.5, 124.9, 124.3, 123.4, 123.3 (Tbf Ar CH); 92.9 (HC=C); 67.8 (—OCH$_2$—); 67.0 and 66.2 (—OCH$_2$—Ar); 49.4 (—OCCH$_2$CO—); 47.0 (allylic C); 33.4, 29.2, 29.0, 28.9, 28.6, 25.6, 22.0 (—CH$_2$—). $\lambda_{max}$/nm ($\delta$/dm$^3$mol$^{-1}$ cm$^{-1}$) 381 (4496), 365 (4496), 301 (12650), 288 (11331), 254 (20504). HRMS (FAB), M$^+$/z C$_{55}$H$_{47}$F$_3$O$_4$ (M$^-$) requires 828.3426; found 828.3424.

Step (h) Preparation of [4-[[10-(17-Tetrabenzo-[a, c, g, i] fluoren-17-yl)decyl]oxy]phenyl]methyl α-[(cyclopropylamino)methylene-(2,4,5-trifluoro-β-oxobenzenepropanoate, 4

To an oven-dried flask was added 4-[[10-(17H-tetrabenzo [a, c, g, i]fluoren-17-yl)-decyl]oxy]phenyl]-methyl 2,4,5-trifluoro-β-oxobenzenepropanoate (6) (122.5 mg, 0.148 mmol) and dissolved in freshly distilled THF (10 mL). The flask was purged with nitrogen and N,N-dimethylformamide diethyl acetal was added as a solution in THF (1 mL) via syringe. Glassware was washed with THF (2 mL). The solution was stirred at room temperature under an atmosphere of nitrogen for 24 hours. Cyclopropylamine (120.2 mg, 0.818 mmol) was added as a solution in THF (1 mL) and the resultant solution stirred at room temperature under nitrogen for 72 hours. The solution was quenched by the addition of saturated ammonium chloride solution (20 mL) and organic products extracted with DCM (2×20 mL), dried over MgSO$_4$ and solvent removed in vacuo to yield a dark yellow oil. This was purified by flash column chromatography using DCM as eluent to yield [4-[[10-(17 H-tetrabenzo [a, c, g, i] fluoren-17-yl)-decyl]oxy]phenyl] methyl α-[(cyclopropylamino)-methylene]-2,4,5-trifluoro-β-oxobenzenepropanoate as a pale yellow solid (45.1 mg, 0.051 mmol, 34%). Rf 0.44 (CH$_2$Cl$_2$), mp 49–51° C. FTIR, $\nu_{max}$/cm$^{-1}$ 3082, 3036, 2930, 2854, 1677, 1623, 1511, 1434, 1326, 1238, 1174, 1140, 1082. $^1$H NMR (CDCl$_3$, 250 MHz), δ/ppm 10.82 and 9.43 (1 H, both d, $^3$J=11.8 Hz); 8.83–8.78 (4 H, m, Ar—H); 8.71–8.66 (2 H, m, Ar—H); 8.28–8.23 (2 H, m, Ar—H); 8.20–8.14 (1 H, t, $^3$J=7.9 Hz, olefinic H); 7.74–7.59 (8 H, m, Ar—H); 7.09–6.61 (6 H, m Ar—H); 5.05 (1 H, t, 3J=4.4 Hz, allylic H); 4.95 and 4.88 (2 H, s, —OCH$_2$—Ar); 3.83 (2 H, t, $^3$J=6.6 Hz, —OCH$_2$); 2.94–2.91 (1 H, m, c—CHCH$_2$CH$_2$); 2.65–2.51 (2 H, m, —OCH$_2$CH$_2$); 1.68–0.34 (20 H, m, alkyl H). $^{13}$C{$^1$H}NMR (CDCl$_3$, 63 MHz), δ/ppm 168.0 (CO$_2$R); 166.4 (C=O); 160.8 (—CH=C); 159.0, 127.4 (quat. Ar C); 155.9, 152.3, 148.4, 117.1, (quat. Ar C); 144.3, 136.7, 131.1, 130.3,.128.7, 127.9, (Tbf quat. Ar C); 129.9, 114.1 (Ar CH); 116.3, 105.0 (Ar CH); 127.4, 127.0, 125.8, 125.5, 124.9, 124.4, 123.4, (Tbf Ar CH); 101.4 (—CH=C); 67.8 (—OCH$_2$—); 65.7 and 65.5 (—OCH$_2$—Ar); 47.1 (allylic C); 33.4, 29.3, 29.1, 29.0, 28.6, 25.7, 22.0 (—CH$_2$—); 30.4 and 30.0 (c—CHCH$_2$CH$_2$); 6.42 (CHCH$_2$CH$_2$). $^{19}$FNMR (CDCl$_3$, 235 MHz) δ/ppm –117, –132, –114 (m, Ar—F). $\lambda_{max}$/nm (δ/dm$^3$mol$^{-1}$cm$^{-1}$) 381 (17916), 364 (18859), 316 (21688), 301 (56106), 289 (44790), 254 (81094), 239 (69307). MS (FAB) M$^+$/z C$_{59}$ H$_{52}$F$_3$NO$_4$ requires 896; found 896.

Step (i) Preparation of [4-[[10-(17H-Tetrabenzo-[a, c, g, i] fluoren-17-yl)decyl]oxy]phenyl]methyl 1-cyclopropyl-6,7-difluoro-1,4-dihydro-4-oxo-3-quinolinecarboxylate, 3

A) From [4-[[10-(17 H-Tetrabenzo [a, c, g, i] fluoren-17-yl)decyl]oxy]phenyl]methyl α-[(cyclopropylamino)-methylene]-2,4,5-trifluoro-β-oxobenzenepropanoate, 4

[4-[[10-(17 H-Tetrabenzo [a, c, g, i] fluoren-17-yl)-decyl] oxy]phenyl]methyl α-[(cyclopropylamino)-methylene]-2,4, 5-trifluoro-β-oxobenzenepropanoate (4) (80.7 mg, 0.090 mmol) was added to an oven-dried flask fitted with a reflux condenser and dissolved in freshly distilled DCM (12 mL). The solution was purged with nitrogen and to it added TMG (207.5 mg, 1.80 mmol). The reaction mixture was then refluxed under an atmosphere of nitrogen for 20 hours before cooling to room temperature and quenching with water (20 mL). The aqueous layer was separated and washed with DCM (2×20 mL). The combined organic fractions were washed with 2 M HCl (20 mL), saturated sodium carbonate solution (20 mL), water (20 mL), and brine (20 mL), dried (MgSO$_4$) and solvent removed in vacuo to yield an orange oil. This was purified by flash column chromatography using ethyl acetate/hexane (5:1) as eluent to yield [4-[[10-(17 H-tetrabenzo [a, c, g, i]-fluoren-17-yl)decyl]oxy]phenyl] methyl 1-cyclopropyl-6,7-difluoro-1,4-dihydro-4-oxo-3-quinolinecarboxylate as a yellow solid (43.4 mg, 0.049 mmol, 55%).

B) From [4-[[10-(17 H-Tetrabenzo [a, c, g, i] fluoren-17-yl)decyl]oxy]phenyl]methyl 2,4,5-trifluoro-β-oxobenzenepropanoate, 1

4-[[10-(17 H-Tetrabenzo [a, c, g, i] fluoren-17-yl)decyl] oxy]phenyl]methyl 2,4,5-trifluoro-β-oxobenzenepropanoate (6) (44.9 mg, 0.054 mmol) was added to a three-necked, oven-dried flask fitted with reflux condenser and dissolved in freshly distilled THF (5 mL). The vessel was purged with nitrogen and N,N-dimethylformamide dimethyl acetal (39.5 mg, 0.326 mmol) was added as a solution in THF (2 mL) via syringe. Glassware was washed with THF (2 mL). The solution was stirred at room temperature under an atmosphere of nitrogen for 24 hours. Cyclopropylamine (36.3 mg, 0.637 mmol) was added as a solution in THF (2 mL) and the resultant solution stirred at room temperature under nitrogen for 24 hours. TMG (122.5 mg, 1.07 mmol) was added as a solution in THF (2 mL) and the reaction mixture refluxed under nitrogen for 20 hours. The solution was cooled to room temperature and quenched with saturated ammonium chloride solution (20 mL). The mixture was filtered through a small pad of silica and washed with ethyl acetate (40 mL). The organic layer was washed with brine (30 mL), dried (MgSO$_4$), and solvent removed in vacuo to yield a dark yellow oil. This was absorbed onto silica and purified by flash column chromatography using ethyl acetate/hexane (5:1) as eluent to yield [4-[[10-(17 H-tetrabenzo [a, c, g, i] fluoren-17-yl)decyl]-oxy]phenyl] methyl 1-cyclopropyl-6,7-difluoro-1,4-dihydro-4-oxo-3-quinolinecarboxylate as a yellow solid (24.7 mg, 0.028 mmol, 52%). Rf 0.53 (EtOAc/hexane, 5:1), mp 71–73° C. FTIR, $\nu_{max}$/cm$^{-1}$ 3071, 2987, 2932, 2854, 1726, 1690, 1643, 1513, 1494, 1287, 1250, 1171, 1087. $^1$ H NMR (CDCl$_3$, 250 MHz), δ/ppm 8.79–8.75 (4 H, m, Ar H); 8.68–8.64 (2 H, m, Ar H); 8.41 (1 H, s, olefinic H); 8.25–8.12 (2 H, m, Ar H); 7.76–7.55 (9 H, m, Ar H): 7.42–7.39 (2 H, m, Ar—H); 6.94–6.71 (3 H, m, Ar H); 5.00 (1 H, t, $^3$J=4.1 Hz, allylic H); 4.92 (2 H, s, —OCH$_2$—Ar); 3.83 (2 H, t, $^3$J=6.5 Hz, —OCH$_2$); 3.24–3.16 (1 H, m, c—CHCH$_2$CH$_2$); 2.62–2.56 (2 H, m, —OCH$_2$CH$_2$—); 1.63–0.33 (20 H, m, alkyl H). $^{13}$C{$^1$H}NMR (CDCl$_3$, 63 MHz), δ/ppm 172.4 (CO$_2$R); 164.8 (C=O); 158.9, 127.9 (quat. Ar C); 148.7 (—CH=C); 155.7, 150.8, 146.54, 137.3, (quat. Ar C); 144.2, 136.6, 131.1, 130.2, 128.6, 127.8, (Tbf quat. Ar C); 129.9, 114.3 (Ar CH); 127.3, 126.7, 125.7, 125.5, 124.9, 124.3, 123.4, 123.3 (Tbf Ar CH); 115.3, 105.4 (Ar CH); 110.5 (—CH=C); 67.7 (—OCH$_2$—); 66.2 (—OCH$_2$—Ar); 47.1 (allylic C); 34.5 (c—CHCH$_2$CH$_2$); 33.3, 29.1, 29.0, 28.9, 28.5, 25.6, 21.9 (—CH$_2$—); 7.9 (CHCH$_2$CH$_2$). $\lambda_{max}$/nm (δ/dm$^3$mol$^{-1}$cm$^{-1}$) 388 (7370), 364 (7830), 331 (9212), 317 (8291), 301 (22110), 289 (19346), 257 (39152), 238 (33164). HRMS (FAB), M$^+$/z C$_{59}$ H$_{52}$F$_2$NO$_4$ (MH$^+$) requires 876.3864; found 876.3860.

Step (j) Preparation of [4-[[10-(17H-Tetrabenzo-[a, c, g,i ] fluoren-17-yl)decyl]oxy]phenyl]methyl 1-cyclopropyl-6-fluoro-1,4-dihydro-4-oxo-7-(1-piperazinyl)-3-quinolinecarboxylate, 2

[4-[[10-(17 H-Tetrabenzo [a, c, g, i] fluoren-17-yl)decyl] oxy]phenyl]methyl 1-cyclopropyl-6,7-difluoro-1,4-dihydro-4-oxo-3-quinolinecarboxylate, 3, (46.2 mg, 0.53 mmol) and piperazine (91.2 mg, 1.06 mmol) were added in pyridine (4 mL) to a flame-dried, round bottomed flask fitted with a condenser and refluxed under nitrogen for 48 hours. The solution was then cooled to room temperature and quenched with saturated ammonium chloride solution (15 mL). Organic products were extracted with DCM (2×20 mL), washed with water (2×20 mL), and dried over $MgSO_4$. Solvent was removed in vacuo to yield a brown oil. This was adsorbed onto silica and purified by column chromatography using $CHCl_3$/methanol (10:1) as eluent to yield a pale yellow solid (48.1 mg, 0.051 mmol, 96%. Rf 0.26 ($CHCl_3$/methanol, 10:1). FTIR $v_{max}$/cm$^{-1}$) ($CH_2Cl_2$): 3073, 3030, 2928, 2855, 1704, 1605, 1579, 1510, 1467, 1390, 1368, 1281, 1240, 1169, 1107, 1021, 849, 816. $\lambda_{max}$/nm ($\delta$/dm$^3$mol$^{-1}$cm$^{-1}$): 380 (11409), 364 (11409), 336 (15772), 323 (14430), 302 (36577), 290 (41946), 281 (33893), 254 (60403).

Step (k) Preparation of 1-Cyclopropyl-6-fluoro-1,4-dihydro-4-oxo-7-(1-piperazinyl)-3-quinoline-carboxylic acid, 1

The compound obtained in Step (j) may be stirred in a solution of TFA/DCM to afford the title compound.

EXAMPLE 4

Interaction of Tbf-derivatives with Carbon
General Procedure

A solution (approximately 5×10$^{-5}$moldm$^{-3}$) of the Tbf-derivative investigated was prepared in 25 mL of the appropriate solvent and the UV-visible spectrum of the solution measured against the solvent background in the region 320 to 420 nm. Carbon was added (charcoal) and the suspension stirred at room temperature for 20 minutes. The UV-visible spectrum of the supernatant was measured to detect adsorption of the Tbf-compound onto the carbon. A lower degree of UV-visible adsorbance indicated adsorption onto carbon. More carbon was added, if required, and the suspension stirred at room temperature for a further 20 minutes. The UV-visible spectrum of the supernatant was remeasured. Carbon addition and stirring was continued until a satisfactory degree of adsorption was detected.

Desorption experiments were initiated by centrifuging the carbon suspension and completely removing the supernatant. A different solvent (25 mL) was added and the carbon suspension sonicated for periods of 20 minutes at 40° C. UV-visible spectra of the supernatant were recorded, against the solvent background, until no more desorption was detected.

4-[[10-(17H-Tetrabenzo [a, c, g, i] fluoren-17-yl)decyl]oxy] benzenemethanol, 8

The general procedure was followed to adsorb 8 (0.55 mg, 875 nmol) onto charcoal (40 mg) using DCM as solvent. UV-visible spectrum indicated an adsorbance of 92% (20 nmol/mg carbon loading). Desorption was carried out using toluene. The maximum level of desorption by UV spectroscopy was 19%. Solvent was removed in vacuo and dioxane added (25 mL). UV spectroscopy after sonication showed a decreased absorbance indicating that readsorption had occurred.

4-[[10-(17H-Tetrabenzo [a, c, g, i] fluoren-17-yl-decyl]oxy] phenyl]methyl 2,4,5-trifluoro-β-oxobenzenepropanoate, 6

1. The general procedure was followed to adsorb 6 (0.54 mg, 658 nmol) onto charcoal (21.3 mg) using DCM as solvent. UV-visible spectrum indicated an adsorbance of 97% (20 nmol/mg carbon loading). Desorption was carried out using ethyl acetate. No desorption was detected by UV.

Similarly for dioxane as solvent. Toluene was used as the solvent. The maximum level of desorption by UV spectroscopy was 27%.

2. The general procedure was followed to adsorb 6 (0.52 mg, 628 nmol) onto charcoal (5.8 mg) using methanol/DCM (4:1). UV-visible spectrum indicated an adsorbance of 92% (99 nmol/mg carbon loading). Desorption was carried out using toluene. The level of desorption by UV spectroscopy was 60%. The supernatant was removed and fresh toluene added. Sonication enabled the desorption of a further 25%, giving a total desorption of 85%.

[4-[[10-(17H-Tetrabenzo [a, c, g, i] fluoren-17-yl)decyl]-oxy]phenyl]methyl 1-cyclopropyl-6,7-difluoro-1,4-dihydro-4-oxo-3-quinolinecarboxylate, 3

1. The general procedure was followed to adsorb 3 (1.4 mg, 1600 nmol) onto charcoal (14.2 mg) using DCM/methanol (3:2) as solvent. UV-visible spectrum indicated an adsorbance of 89% (100 nmol/mg carbon loading). Desorption was carried out using toluene as the solvent. The maximum level of desorption by UV spectroscopy was 18%.

2. The general procedure was followed to adsorb 3 (1.4 mg, 1600 nmol) onto charcoal (19.9 mg) using DCM/methanol (3:2) as solvent. UV-visible spectrum indicated an adsorbance of 93% (75 nmol/mg carbon loading). Desorption was carried out using THF as the solvent. The maximum level of desorption by UV spectroscopy was 10%.

EXAMPLE 5

Reactions on Carbon Solid Support
Preparation of [4-[[10-(17H-Tetrabenzo [a, c, g, i] fluoren-17-yl)decyl]oxy]phenyl]methyl 1-cyclopropyl-6,7-difluoro-1,4-dihydro-4-oxo-3-quinolinecarboxylate, 3

[4-[[10-17H-Tetrabenzo [a, c, g, i] fluoren-17-yl)-decyl]oxy]phenyl]methyl 2,4,5-trifluoro-β-oxobenzenepropanoate (6) (21.0 mg, 0.025 mmol) was dissolved in DCM/methanol (3:2, 50 mL) and adsorbed onto activated charcoal (210 mg). Supernatant was removed and the charcoal residue suspended in freshly distilled THF (30 mL) in an oven-dried, three-necked flask fitted with a reflux condenser. The vessel was purged with nitrogen and N,N-dimethylformamide dimethyl acetal (30.5 mg, 0.252 mmol) was added as a solution in THF (2 mL) via syringe. Glassware was washed with THF (2 mL). The solution was stirred at room temperature under an atmosphere of nitrogen for 24 hours. Cyclopropylamine (14.0 mg, 0.246 mmol) was added as a solution in THF (2 mL) and the resultant solution stirred at room temperature under nitrogen for 72 hours. TMG (57.8 mg, 0.503 mmol) was added as a solution in THF (2 mL) and the reaction mixture refluxed under nitrogen for 30 hours. The solution was cooled to room temperature and methanol (60 mL) added. The mixture was stirred at room temperature for 20 minutes, after which time, no fluorescent products were detected by TLC. The supernatant was removed and the carbon residue sonicated in toluene (4×70 mL). Supernatants were combined and solvent removed in vacuo to yield a dark yellow oil. This was adsorbed onto silica and purified by flash column chromatography using ethyl acetate/hexane (5:1) as eluent to yield two products (both fluorescent). Rf 0.82, 7.7 mg, submitted FABMS. Rf 0.55 (co-elutes with desired product), 9.9 mg, 0.011 mmol, 44%), submitted FABMS.

Preparation of [4- [[10-(17H-Tetrabenzo [a, c, g, i]-fluoren-17-yl)decyl]oxy]phenyl]methyl 1-cyclopropyl-6,7-difluoro-1,4-dihydro-4-oxo-3-quinolinecarboxylate, 3

[4-[[10-(17 H-tetrabenzo [a, c, g, i] fluoren-17-yl)-decyl] oxy]phenyl]methyl 2,4,5-trifluoro-β-oxobenzenepropanoate (6) (25.3 mg, 0.031 mmol) was dissolved in DCM/methanol (3:2, 50 mL) and adsorbed onto activated charcoal (280 mg). Supernatant was removed and the charcoal residue suspended in freshly distilled THF (30 mL) in an oven-dried, three-necked flask fitted with a reflux condenser. The vessel was purged with nitrogen and N,N-dimethylformamide dimethyl acetal (37.7 mg, 0.312 mmol) was added as a solution in THF (2 mL) via syringe. The solution was stirred at room temperature under an atmosphere of nitrogen for. 18 hours. Cyclopropylamine (26.4 mg, 0.463 mmol) was added as a solution in THF (2 mL) and the resultant solution stirred at room temperature under nitrogen for 24 hours. TMG (71.6 mg, 0.623 mmol) was added as a solution in THF (2 mL) and the reaction mixture refluxed under nitrogen for 24 hours. The solution was cooled to room temperature and methanol (60 mL) added. The mixture was stirred at room temperature for 20 minutes after which time, no fluorescent products were detected by TLC. The supernatant was removed and the carbon residue suspended in a solution of piperazine (56.4 mg, 0.641 mmol) in NMP (30 mL). The mixture was stirred at 110° C. under an atmosphere of nitrogen for 4 hours, after which time the suspension was cooled to room temperature and methanol (60 mL) added. After stirring for 30 minutes, the supernatant was removed and the charcoal residue sonicated in toluene (4×70 mL); monitoring each wash by UV. Extracts were combined and solvent removed in vacuo to yield a dark yellow oil. This was purified by flash column chromatography using ethyl chloroform/methanol (20:1) as eluent to yield two products (both fluorescent). Rf 0.82, 10.2 mg, submitted FABMS. Rf 0.50, 6.3 mg, submitted FABMS.

What is claimed is:

1. A method for synthesizing a library of quinolone compounds of the formula:

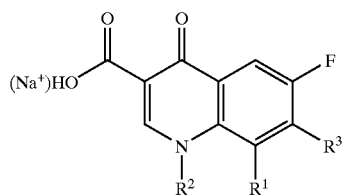

wherein $R^1$ is H or F;

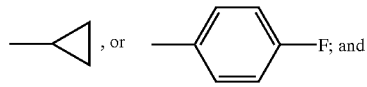

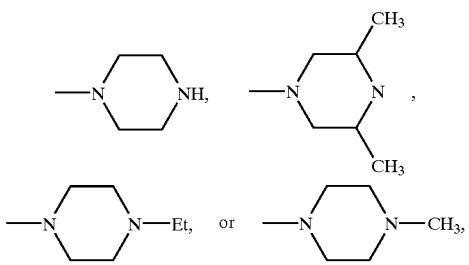

which comprises:

Step (a) reacting a building block containing tetrabenzo [a, c, g, i] fluorene group (Tbf-A) of the formula:

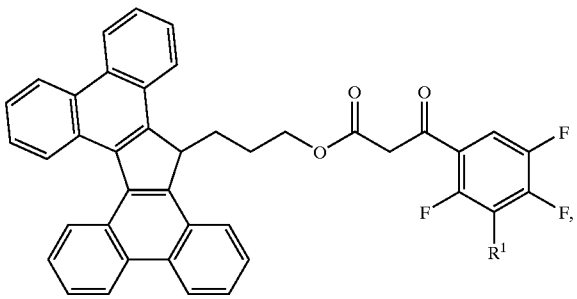

with a building block B of the formula $NH_2R_2$ to form Tbf-A-B;

Step (b) purifying the intermediate compound (Tbf-A-B), by adsorption on charcoal;

Step (c) removing the intermediate compound (Tbf-A-B), from the charcoal with toluene;

Step (d) repeating steps (a)–(c) using a number of building blocks to synthesize said library of compounds containing THF groups; and Step (e) removing the Tbf groups from the compounds by adsorption on charcoal and subsequently adding a cleaving reagent in a solvent to form said library of compounds.

2. A method according to claim 1 wherein the compound is ciprofloxacin.

* * * * *

UNITED STATES PATENT AND TRADEMARK OFFICE
CERTIFICATE OF CORRECTION

PATENT NO. : 6,566,520 B2
DATED : May 20, 2003
INVENTOR(S) : DeWitt et al.

It is certified that error appears in the above-identified patent and that said Letters Patent is hereby corrected as shown below:

<u>Column 4,</u>
Line 43, insert
-- BRIEF DESCRIPTION OF THE DRAWINGS
The Figure shows studies of the binding affinity of the Tbf-bound $\beta$-keto ester. --

<u>Column 8,</u>
Line 36, "Scheme 4" should read -- Figure 1 --
Line 38, "Scheme 5" should read -- Scheme 4 --

<u>Column 18,</u>
Line 59, "(233 30 mL)" should read -- (2x30 mL) --

<u>Column 19,</u>
Lines 29-30, "(3x5 mL)," should read -- (3x50 mL), --
Line 49, "($\delta$/dm$^3$mol$^{-1}$cm$^{-1}$)" should read -- ($\epsilon$/dm$^3$mol$^{-1}$cm$^{-1}$) --

<u>Column 20,</u>
Line 20, "($\delta$/dm$^3$mol$^{-1}$cm$^{-1}$)" should read -- ($\epsilon$/dm$^3$mol$^{-1}$cm$^{-1}$) --
Line 60, "(CDC1$_1$, 63 MHz)," should read -- (CDC1$_3$, 63 MHz), --

<u>Column 21,</u>
Lines 1-2, "($\delta$/dm$^3$mol$^{-1}$cm$^{-1}$)" should read -- ($\epsilon$/dm$^3$mol$^{-1}$cm$^{-1}$) --
Line 50, "($\delta$/dm$^3$mol$^{-1}$cm$^{-1}$)" should read -- ($\epsilon$/dm$^3$mol$^{-1}$cm$^{-1}$) --

<u>Column 22,</u>
Line 60, "($\delta$/dm$^3$mol$^{-1}$cm$^{-1}$)" should read -- ($\epsilon$/dm$^3$mol$^{-1}$cm$^{-1}$) --

<u>Column 23,</u>
Line 17, "($\delta$/dm$^3$mol$^{-1}$cm$^{-1}$)" should read -- ($\epsilon$/dm$^3$mol$^{-1}$cm$^{-1}$) --

UNITED STATES PATENT AND TRADEMARK OFFICE
CERTIFICATE OF CORRECTION

PATENT NO. : 6,566,520 B2
DATED : May 20, 2003
INVENTOR(S) : DeWitt et al.

It is certified that error appears in the above-identified patent and that said Letters Patent is hereby corrected as shown below:

Column 25, line 44 through Column 26, line 8,
"wherein $R^1$ is H or F;

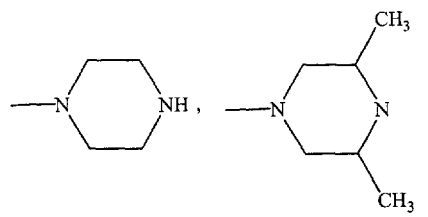

"

should read
-- wherein $R^1$ is H or F;

$R^2$ is 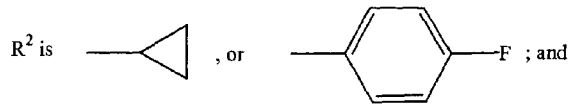

$R^3$ is 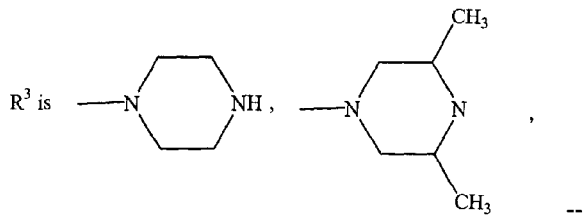

--

UNITED STATES PATENT AND TRADEMARK OFFICE
CERTIFICATE OF CORRECTION

PATENT NO.    : 6,566,520 B2
DATED         : May 20, 2003
INVENTOR(S)   : DeWitt et al.

It is certified that error appears in the above-identified patent and that said Letters Patent is hereby corrected as shown below:

Column 26,
Line 16, "tetrabenzo" should read -- tetrabenzole --
Line 41, "THF" should read -- Tbf --

Signed and Sealed this

Twenty-eighth Day of October, 2003

JAMES E. ROGAN
*Director of the United States Patent and Trademark Office*